United States Patent [19]

Shih et al.

[11] Patent Number: 5,563,292

[45] Date of Patent: Oct. 8, 1996

[54] LIPOXYGENASE INHIBITORS

[75] Inventors: Neng-Yang Shih, North Caldwell, N.J.; Pietro Mangiaracina, Monsey, N.Y.

[73] Assignee: Schering Corporation, Kenilworth, N.J.

[21] Appl. No.: 847,071

[22] PCT Filed: Oct. 17, 1990

[86] PCT No.: PCT/US90/05824

§ 371 Date: Apr. 2, 1992

§ 102(e) Date: Apr. 2, 1992

[30] Foreign Application Priority Data

Oct. 17, 1990 [WO] WIPO ...................... PCT/US90/05824

[51] Int. Cl.$^6$ ...................................... C07C 67/02
[52] U.S. Cl. .............. 560/255; 560/1; 560/100; 560/53; 560/105; 560/106; 560/163; 560/312; 562/463; 562/621; 568/425; 568/659; 568/662; 568/807
[58] Field of Search ...................... 560/255, 100, 560/105, 106, 163, 312, 53, 1; 562/463, 621; 568/425, 659, 662, 807; 514/570, 546

[56] References Cited

U.S. PATENT DOCUMENTS 4,584,320  4/1985  Rubin .
4,708,964  11/1987  Allen .

FOREIGN PATENT DOCUMENTS

81/03021  10/1981  WIPO .
8803800  6/1988  WIPO .

OTHER PUBLICATIONS

Asahara et al Bull. Jap. Petrol Insl. 12 49–53 1970.

*Primary Examiner*—Paul J. Killos
*Attorney, Agent, or Firm*—Henry C. Jeanette

[57] ABSTRACT

Novel compounds of Formula 1

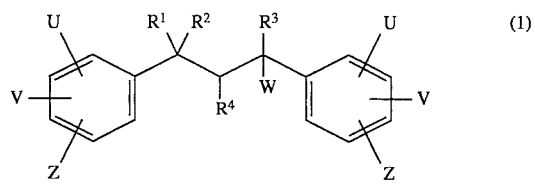

or a pharmaceutically acceptable salt or solvate thereof are disclosed.

Also disclosed are pharmaceutical compositions containing compounds of Formula 1. Methods of treating allergy, inflammation and hyperproliferative skin diseases with compounds of Formula 1 are also disclosed.

10 Claims, No Drawings

LIPOXYGENASE INHIBITORS

FIELD OF THE INVENTION

This invention relates to certain phenyl-alkylphenyl compounds which are useful as inhibitors of the lipoxygenase pathways in the metabolism of arachidonic acid.

BACKGROUND OF THE INVENTION

A number of lipoxygenase inhibitors are known. For example, International Application Number PCT/US86/02548, International Publication Number WO 88/03800 published Jun. 2, 1988 discloses compounds having the formula:

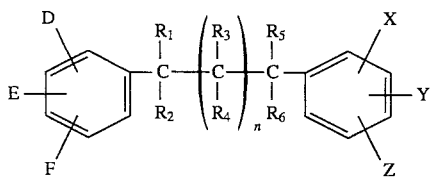

wherein D, E, F, X, Y, Z, may be H; OH; O-alkyl; or O-acyl optionally substituted with hydroxy, alkoxy, substituted amino, carboxyl, or carbalkoxyl; $R_1$ to $R_6$ may be H; lower alkyl or lower alkoxyl optionally substituted with hydroxy, alkoxy, substituted amino, carboxyl, or carbalkoxyl; carbonyl; alkoxy; aryl; or aralkyl; and n may be 0 to 5.

Arachidonic acid is metabolized by means of the enzymes 5-lipoxygenase and cyclooxygenase into various leukotrienes, including slow reacting substances, and prostaglandins which cause allergic reactions, inflammation and hyperproliferative skin diseases. Inhibition of the activity of 5-lipoxygenase (5-LO) reduces the manifestation of the symptoms of allergic reactions, e.g. chronic obstructive lung disease such as asthma, allergic or seasonal rhinitis, bronchitis, and the like; inflammatory diseases such as arthritis, bursitis, tendonitis, gout and inflammatory bowel disease; hypoproliferative skin disease, a symptom of which is accelerated skin cell production manifested by flaking, scales or papular lesions, e.g., psoriasis, lichenified eczema, dandruff, and the like.

A welcome contribution to the art would be novel organic compounds which are useful as lipoxygenase inhibitors. Such a contribution is provided by this invention.

SUMMARY OF THE INVENTION

This invention provides compounds having particularly advantageous properties useful in the treatment of inflammatory and allergic reactions by inhibiting the formation of 5-lipoxygenase derived products of arachidonic acid metabolism. One embodiment of this invention provides compounds represented by Formula 1:

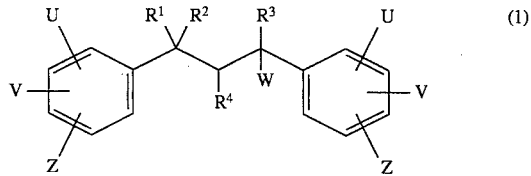

or a pharmaceutically acceptable salt or solvate thereof wherein:

(A) $R^1$ and $R^2$ are the same or different and are selected from:

(1) alkyl;

(2) substituted alkyl wherein the substituent is selected from aryl, substituted aryl, heteroaryl, —$OR^5$, and —$NR^6R^7$;

(3) cycloalkyl;

(4) aryl;

(5) substituted aryl wherein one or more of the ring hydrogens are independently substituted by substituents selected from alkyl and —O-alkyl; and (6) heteroaryl;

(B) $R^3$ and $R^4$ are the same or different and are independently selected from H, $R^1$ and $R^2$;

(C) U, V, and Z are the same or different and are independently selected from H, $R^1$, $R^2$, —$OR^{10}$, —$O(CH_2)_mR^8$, —$OC(O)R^9$, and —$OC(O)NR^6R^7$; and (D) W is —$(CH_2)_nX$ wherein X is selected from:

(1) —$OR^{10}$ (2) —$OC(O)R^9$;

(3) —$OC(O)NR^6R^9$;

(4) —$NR^6R^7$;

(5) —$N(OH)C(O)R^{10}$; and (6) —$C(O)R^{11}$ n is an integer from 1 to 8;

wherein $R^5$ is selected from H, alkyl, aryl, alkaryl, aralkyl, cycloalkyl, and heteroaryl with the proviso that said heteroaryl group is bound through a ring carbon;

$R^6$ and $R^7$ are the same or different and are independently selected from H, alkyl, aryl, aralkyl, acyl substituted aryl, cycloalkyl and heteroaryl, with the proviso that when $R^6$ and/or $R^7$ is a heteroaryl group said heteroaryl group is bound by a ring carbon;

$R^8$ is selected from aryl, substituted aryl, and heteroaryl, with the proviso that said heteroaryl group is bound through a ring carbon;

$R^9$ is selected from H, alkyl, aryl, substituted aryl, aralkyl, cycloalkyl, and heteroaryl, with the proviso that said heteroaryl group is bound through a ring carbon;

m is an integer from 1 to 4;

$R^{10}$ is selected from H and alkyl; and.

$R^{11}$ is selected from H, —$OR^5$, —$NR^6R^7$, and —$NR^5OH$.

Preferred compounds of this invention are represented by Formula 2:

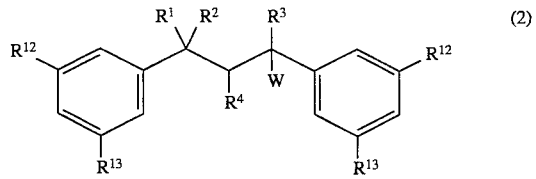

wherein $R^{12}$ and $R^{13}$ are the same or different and are independently selected from U, V, and Z as defined for Formula 1 and $R^1$, $R^2$, $R^3$, $R^4$ and W are as defined for Formula 1.

More preferred compounds of this invention are represented by Formula 3:

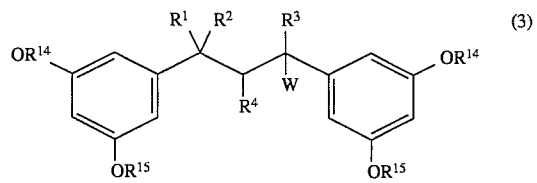

wherein $R^{14}$ and $R^{15}$ are the same or different and are independently selected from H, and alkyl and $R^1$, $R^2$, $R^3$, $R^4$, and W are as defined for Formula 1.

The most preferred compounds of this invention are represented by Formula 4:

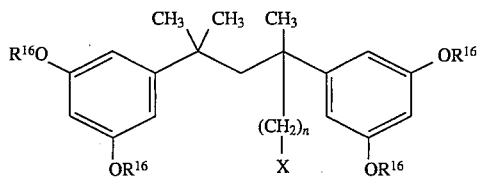

wherein X and n are as defined for Formula 1 and each $R^{16}$ is independently selected from hydrogen or methyl.

Preferred compounds of Formula 4 are represented by Formulas 5 and 6:

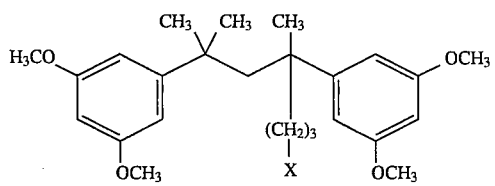

wherein X is selected from —C(O)H, —C(O)OH, —C(O)OCH3 and —C(O)NHOH, and

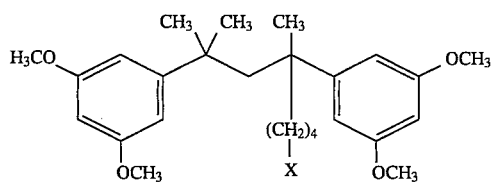

wherein X is selected from —OH and —OC(O)CH$_3$.

Preferably $R^1$ and $R^2$ are independently selected from alkyl, substituted alkyl, aryl and substituted aryl—i.e., aryl substituted with at least one group selected from halo, alkyl, hydroxy, alkoxy, phenoxy, amino, alkylamino, and dialkylamino. Most preferably $R^1$ and $R^2$ are the same and represent an alkyl group having from 1 to 3 carbon atoms, and even more preferably the alkyl group is a methyl group.

Preferably $R^3$ and $R^4$ are independently selected from H, alkyl, substituted alkyl, aryl and substituted aryl wherein there is at least one substituent, and said substituents are as defined for Formula 1. Most preferably $R^3$ is an alkyl group having from 1 to 3 carbon atoms, preferably methyl, and $R^4$ is H.

Preferably U, V, and Z are selected from H, —OR$^5$, —OR$^7$, —O(CH$_2$)$_m$R$^8$, OC(O)R$^9$, O(CO)NR$^5$R$^9$ and aryl, wherein $R^9$ is selected from alkyl, aryl and substituted aryl wherein there is at least one substituent as defined for Formula 1. Most preferably U, V, and Z are each independently selected from H, —OR$^5$, and —OR$^7$. Even more preferably one of U, V, and Z is hydrogen and the others are independently selected from —OR$^5$ and —OR$^7$ wherein $R^5$ and $R^7$ are independently selected from H and alkyl. Still more preferably one of U, V, and Z is hydrogen and the others are —OR$^5$ wherein each $R^5$ is the same alkyl group, with methyl being the most preferred alkyl group.

Preferably when n is 3, X is —C(O)R$^{11}$, when n is 4, X is selected from —OR$^{10}$, —OC(O)R$^9$, —N(OH)C(O)R$^{10}$ and —NR$^6$R$^7$.

More preferably X is selected from —C(O)H, —C(O)OH, —C(O)OCH$_3$, and —C(O)NHOH when n is 3, and when n is 4, X is selected from —OR$^{10}$ and —OC(O)R$^9$ wherein $R^9$ and $R^{10}$ are as defined for Formula 1. Even more preferably, when n is 4, X is selected from —OH and —OC(O)CH$_3$.

This invention also provides a method of inhibiting 5-lipoxygenase metabolism of arachidonic acid by administering a composition comprising an effective amount of a compound of Formula 1 to a patient in need of such treatment.

In addition, this invention also provides a method of treating allergies, inflammation and/or hyperproliferative skin diseases by administering to a patient in need of such treatment a compound of Formula 1.

When treating allergic reactions, the preferred mode of administration of the compounds of this invention is oral. The preferred dosage amounts are about 10 to 500 mg per day, preferably in a single dose, although divided doses can be used.

When treating inflammation, the preferred mode of administration of the compounds of this invention is oral. The preferred dosage amounts are 10 to 500 mg per day, preferably in a single dose, although divided doses can be used.

When treating hyperproliferative skin diseases such as psoriasis, the preferred mode of administration is topical. The preferred concentration of active compound of this invention in pharmaceutically acceptable topical compositions is from about 0.10 to about 10 percent by weight.

Preferred compounds for use in this invention are:
(a) 5,7-dimethyl-5,7-bis(3,5-dimethoxyphenyl)-1-octanol;
(b) 5,7-dimethyl-5,6-di(3,5-dimethoxyphenyl)-octan-1-acetate;
(c) 5,7-dimethyl-5,7-di-(3,5-dimethoxyphenyl)-octanal;
(d) 5,7-dimethyl-5,7-di-(3,5-dimethoxyphenyl)-methyloctanoate;
(e) 5,7-dimethyl-5,7-di-(3,5-dimethoxyphenyl)-N-hydroxyoctamide.

Most preferred is 5,7-dimethyl-5,7-bis(3,5-dimethoxyphenyl)-1-octanol.

DETAILED DESCRIPTION OF THE INVENTION

When used herein, the terms listed below have the following meanings, unless indicated otherwise in the text:

"alkyl" means straight or branched saturated carbon chains, which contain from 1 to 6 carbon atoms such as methyl, ethyl, propyl, iso-propyl, butyl, t-butyl, dimethyl butyl and the like. The preferred alkyl is methyl;

"acyl" means —C(O)-alkyl, —C(O)-alkenyl, —C(O)-alkynyl, —C(O)-cycloalkyl, —C(O)-cycloalkenyl or —C(O)-cycloalkynyl;

"alkaryl" means an aryl group, as defined below, in which an alkyl group, is substituted for one or more of the aryl H atoms;

"alkenyl" means straight or branched carbon chains having at least one carbon to carbon double bond and preferably having from 2 to 6 carbon atoms;

"aralkyl" means an alkyl group, as defined above, in which an aryl group as defined below is substituted for one of the alkyl H atoms for example, benzyl, phenethyl and the like;

"aralkyloxy" means an aralkyl as defined above, which is attached to a molecule by an oxygen atom (—O-aralkyl) such as benzyloxy;

"aroyl" means C(O)-aryl wherein aryl is as defined below. The preferred aroyl moiety is benzoyl;

"aryl" means a carbocyclic group containing from 6 to 15 carbon atoms and having at least one aromatic ring (e.g., a phenyl or fused ring), all available substitutable carbon atoms being intended as possible points of attachment, said carbocyclic group being optionally substituted at one or more of all available substitutable carbons with up to 3 groups, each independently selected from halo, alkyl (i.e. alkaryl), hydroxy, alkoxy, phenoxy, amino, alkylamino and dialkylamino. Preferred unsubstituted aryl is the phenyl moiety and preferred substituted aryl is dimethoxy phenyl;

"carboxyl" means a hydrocarbyl group which contains at least one C(O)OH group;

"cycloalkenyl" means a carbocyclic ring having from 3 to 8 carbon atoms and at least one carbon to carbon double bond in the ring;

"cycloalkyl" means a saturated carbocyclic ring having from 3 to 8 carbon atoms;

"halo" means fluoro, chloro, bromo or iodo with fluoro, chloro and bromo being preferred;

"heteroaryl" (including the heteroaryl portion of heteroarylmethyl) means heterocyclic aromatic, i.e. cyclic groups having at least one O, S or N heteroatom interrupting a carbocyclic ring structure and having a sufficient number of delocalized pi electrons to provide aromatic character, said rings preferably containing from 2 to 14 carbon atoms, e.g., 2-, 3- and 4-pyridyl, 2- and 3-furyl, 2- and 3-thienyl, 2-, 4- and 5-thiazolyl, 2-, 4- and 5-imidazolyl, 2-, 4- and 5-pyrimidinyl, 2-pyrazinyl, 3- and 4-pyridazinyl, 3-, 5- and 6-[1,2,4-triazinyl], 3- and 5-[1,2,4-thiadizolyl], 2-, 3-, 4-, 5-, 6- and 7-benzofuranyl, 2-, 3-, 4-, 5-, 6- and 7-indolyl, 3-, 4- and 5-pyrazolyl, 2-, 4- and 5-oxazolyl, etc. Preferred heteroaryl groups are 2-, 3- and 4- pyridyl, 2- and 3-furyl, and 3-thienyl, 2-, 4- and 5-imidazolyl and 7-indolyl;

"heterocyclyl" means a substituted or unsubstituted non-aromatic ring containing from 2 to 6 carbon atoms, which may optionally contain at least one carbon-to-carbon double or triple bond, and which contains at least one heteroatom selected from nitrogen, oxygen or sulfur; representative examples of such heterocycles include, but are not limited to: pyrrolidone, piperidine, piperazine, heptamethyleneimine, hexamethyleneimine, homopiperazine, perhydroindole, azetidine, 4-piperidinopiperidine, 1-azacycloheptane, perhydroisoquinoline, decahydroquinoline, 1-phenylpiperazine, 4-phenylpiperidine, 1-(4-fluorophenyl)piperazine, 1,3,5-hexahydrotriazine, glycoluril (acetyleneurea), morpholine, phenylmorpholine, thiomorpholine, propylene sulfide, tetrahydrothiophene, thiazolidine, ω-thiocaprolactam, 1,4-thioxane, 1,3-dithiane, 1,4,7-trithiacyclononane, 1,3,5-trithiane, pentamethylene sulfide, 1,5-dithiacyclooctan-3-ol, 1,4-dithiaspiro[4.5]decan-8-ol, ethylene sulfide, tetrahydrofuran, tetrahydropyran, 2,4,8,10-tetraoxaspiro[5.5]undecane, trimethylene oxide, 1,3,5-trioxane, oxepane, and the like.

Certain compounds of this invention may exist in isomeric forms. The invention contemplates all such isomers both in pure form and in admixture, including racemic mixtures.

Certain compounds of the invention can exist in unsolvated as well as solvated forms, including hydrated forms, e.g., hemihydrate. In general, the solvated forms, with pharmaceutically acceptable solvents such as water, ethanol and the like are equivalent to the unsolvated forms for purposes of the invention.

Certain compounds of the invention will be acidic in nature, e.g., those compounds which possess a carboxyl or phenolic hydroxyl group. These compounds may form pharmaceutically acceptable metal and amine salts. Examples of such metal salts are the sodium, potassium, calcium, aluminum, gold and silver salts. Examples of such amine salts are those formed with pharmaceutically acceptable amines such as ammonia, alkylamines, hydroxyalkylamines, N-methylglucamine and the like.

Certain compounds of the invention e.g., those with a basic —NR⁶R⁷ group, also form pharmaceutically acceptable salts with organic and inorganic acids. Examples of suitable acids for such salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those skilled in the art. The salts are prepared by contacting the free base form with a sufficient amount of the desired acid to produce a salt in the conventional manner. The free base forms may be regenereated by treating the salt with a suitable dilute aqueous base solution such as dilute aqueous sodium hydroxide, potassium carbonate, ammonia and sodium bicarbonate. The free base forms differ from their respective salt forms somewhat in certain physical properties, such as solubility in polar solvents, but the salts are otherwise equivalent to their respective free base froms for purposes of this invention.

The compounds of Formula 1 can be prepared by the processes described below. In these processes the substituents are as described above, unless indicated otherwise. Those skilled in the art will appreciate that in the processes described below the reactions are carried out at a temperature high enough to allow the reaction to proceed at a reasonable rate, but not so high as to cause undue degradation of reactants and/or products. Those skilled in the art will also appreciate that in the following reactions the desired products may be isolated by techniques well known in the art such as distillation, column chromatography, recrystallization, and the like.

Equation (abbreviated "EQ") A depicts a method of preparing compounds of Formula 1 wherein W is —(CH₂)₄OH.

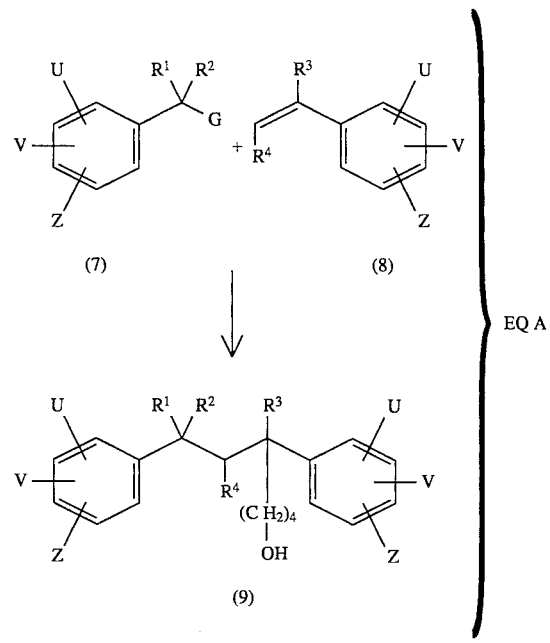

EQ A

In EQ A, compounds represented by Formula 7, wherein G is Br or Cl, are reacted with compounds represented by Formula 8 to produce compounds represented by Formula 9 where R¹ to R⁴ are defined as in Formula 1, U, V, Z are defined as above except OH, OC(O)R⁹ and OC(O)NR⁶R⁷ are not included. The reaction in EQ A takes place at about room temperature (about 20° C.) to 50° C. using tetrahydrofuran (THF) and reactive magnesium. The reactive magnesium is prepared by refluxing K, MgCl$_2$ and KI together in THF in accordance with known procedures (see, for example, *Organic Synthesis*, 1979, Vol. 59, p. 85). In Formula 7, G is a halo atom, with Cl or Br being preferred.

Equation B depicts a method for preparing compounds by converting the —(CH$_2$)$_4$OH moiety to —(CH$_2$)$_4$ alkyl.

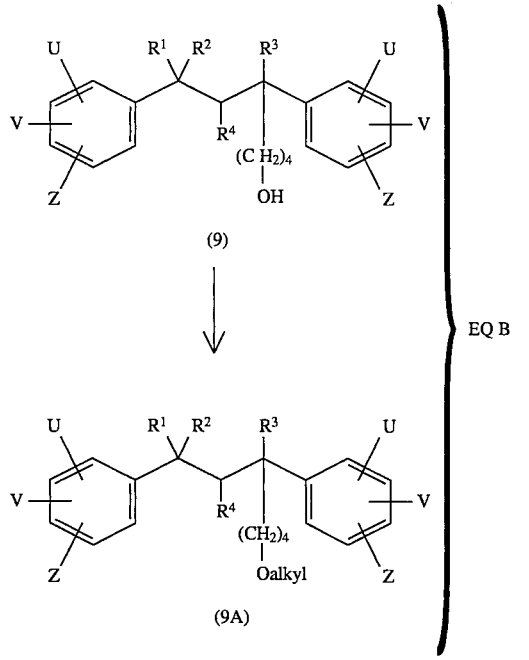

In EQ B, a compound represented by Formula 9 is reacted with alkylX, where X is a halogen atom, with Br or I being preferred. The reaction takes place in a base and an inert aprotic polar organic solvent. The reaction is carried out at a temperature within the range of about 20° C. to refluxing (the boiling point of the organic solvent). The base may be NaH, t-BuOK, Na or CH$_3$Li. The organic solvent may be selected from tetrahydrofuran (THF), dimethylformamide (DMF), dimethoxyethane (DME) and dimethylsulfoxide (DMSO).

EQ C depicts a method of preparing compounds of Formula 1 wherein X is —OC(O) R$^9$ or —OC(O)NR$^5$R$^9$ wherein R$^5$ and R$^9$ are as defined for compound 1.

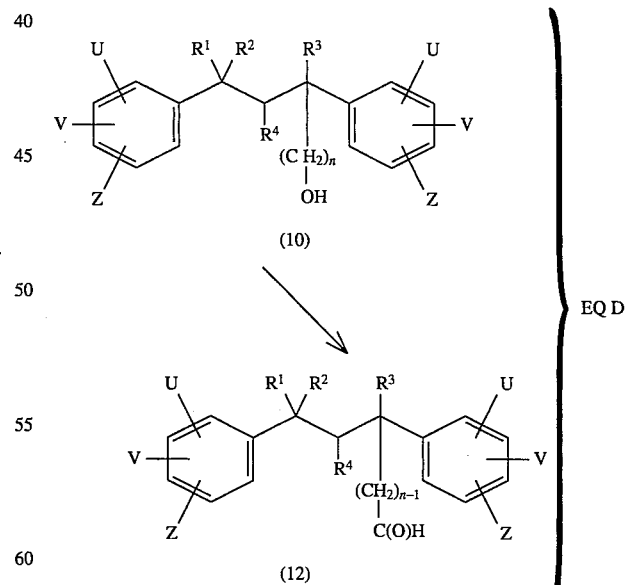

In EQ C, a compound represented by Formula 10 is reacted with ClC(O)Y, where Y= R$^9$ or NR$^6$R$^7$. The reaction takes place in a base and an inert organic solvent (when pyridine is used, it acts as a base and a solvent). The reaction is carried out at a temperature within the range of about −20° C. to about 50° C. The base may be any suitable organic base such as pyridine, 4-dimethylaminopyridine, triethylamine and the like. Preferably triethylamine is used. The inert organic solvent may be selected from CH$_2$Cl, CHCl$_3$, benzene, and pyridine, and the like. When pyridine is used as solvent no other base is needed. Preferably, the reaction is carried out at a temperature of about 0° C. to about 20° C.

EQ D represents a method for preparing compounds of Formula 1 wherein X is —C(O)H.

In EQ D, a compound represented by Formula 10 is reacted with an oxidative agent. The reaction takes place in an inert organic solvent. Usually the reaction is carried out at a temperature of about 0° C. to about 25° C. Examples of oxidative agents include but are not limited to $CrO_3/H_2SO_4$, pyridinium dichromate, $DMSO/COCl_2$, pyridinium chlorochromate, and the like. Preferably, pyridium dichromate is used. Examples of inert organic solvents include benzene, dimethyl formamide, dichloromethane and the like. Preferably, dichloromethane is used. When pyridinium dichromate and dichloroethane are used the reaction may conveniently be carried out at room temperature (20° C.).

EQ E represents a method for preparing compounds of Formula 1 wherein X is $-NR^6R^7$.

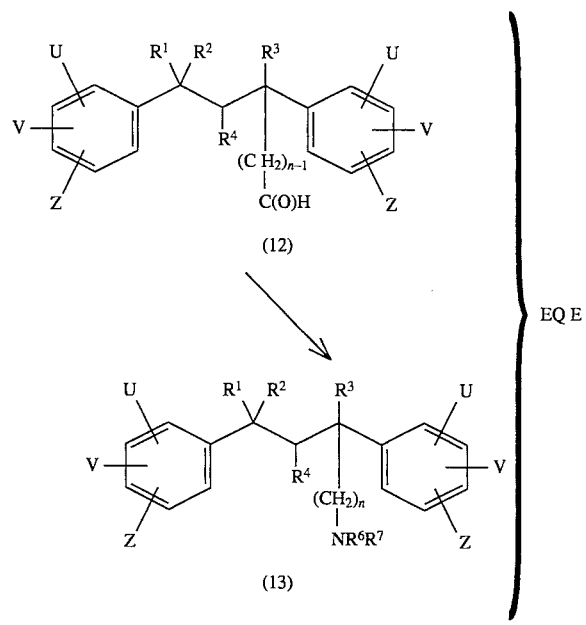

In EQ E, a compound represented by Formula 12 is reacted with an amine, $HNR^6R^7$, and subsequently reduced to produce a compound represented by Formula 13. The reaction is carried out with a reducing agent such as $NaBH_4$, $NaBH_3(CN)$, and the like. Preferably $NaBH_3(CN)$ is used. The reaction is also carried out at a pH in the range of about 4 to about 8. Preferably a pH of about 6 is used when $NaBH_3(CN)$ is used. The pH may be adjusted utilizing standard methods known in the art. The reaction is carried out at a temperature in the range of about 0° C. to about 25° C.

EQ F depicts a method of preparing compounds of formula 1 wherein X is $-N(-OH)C(O)R^{10}$, wherein $R^{10}$ is as defined in the compound of formula 1.

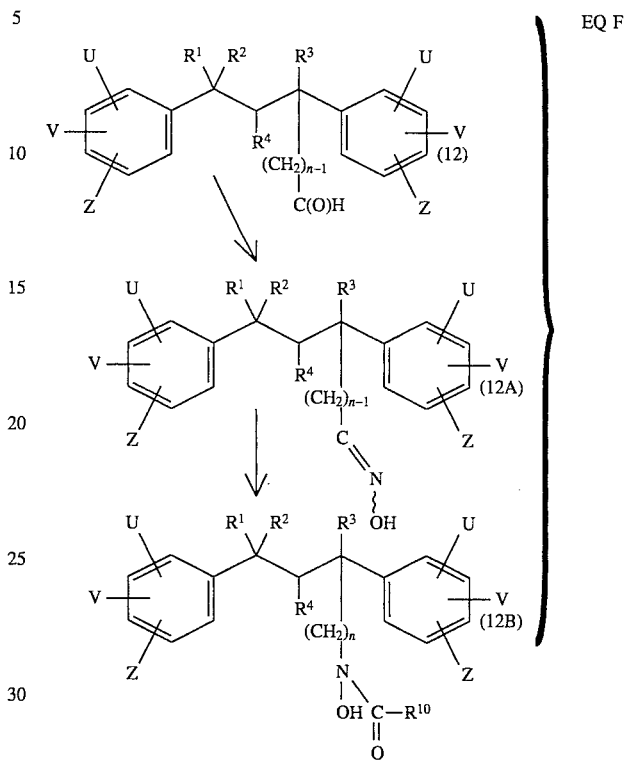

In EQ F, a compound of formula 12 is reacted with hydroxylaminehydrochloride ($NH_2OH \cdot HCl$) to produce a compound represented by Formula 12A. This reaction is carried out in an inert alcoholic solvent, usually ethanol, at a temperature about in the range of about 50° C. to 100° C. in the presence of base such as pyridine or sodium acetate. Conversion of compound 12A to compound 12B can be achieved by following a known procedure as described in Journal of Medicinal Chemistry, Vol. 31, p.3 (1988).

EQ G depicts a method for preparing compounds of Formula 1 wherein X is $-C(O)OH$, from either a compound of formula 10 or a compound of formula 12. EQ G also depicts a method for preparing an intermediate (Formula 15) to other compounds of Formula 1.

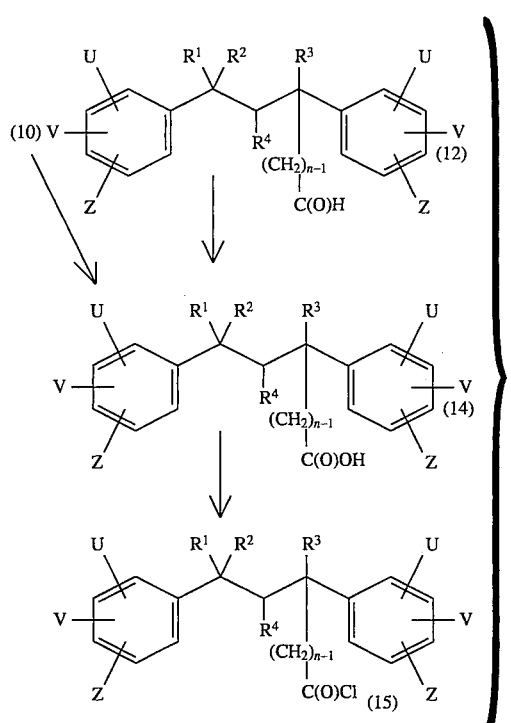

In EQ G a compound of Formula 10 or 12 is reacted with an oxidizing agent to produce a compound of Formula 14. The reaction takes place in an inert organic solvent. Examples of oxidizing agents include AgO, PDC (pyridinium dichromate), KMnO$_4$, and the like. Preferably PDC is used. Examples of inert organic solvents include THF, DMF, acetone and the like. Preferably DMF or acetone is used. The reaction is usually carried out at a temperature of about 0° C. to about 50° C. with about 20° C. being preferred.

The compounds of Formula 14 (EQ G) may be reacted with a halogenating agent to produce a compound of Formula 15. Preferably a chlorinating agent, such as PCl$_5$, SOCl$_2$, (COCl)$_2$, and the like. Preferably SOCl$_2$ or (COCl)$_2$ is used. The reaction takes place in an organic solvent such as dichloromethane, benzene, and the like. The reaction is usually carried out at a temperature of about 0° C. to about 80° C.

EQ H depicts a method for preparing compounds of Formula 1 wherein X is —C(O)OR$^5$.

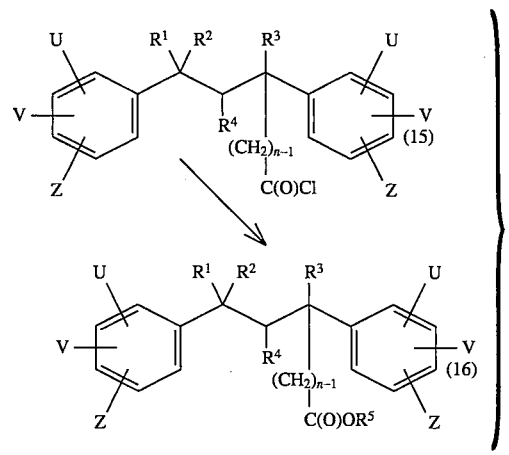

In EQ H, a compound of Formula 15 is reacted with R$^5$OH, wherein R$^5$ is as defined for Formula 1 to produce a compound of Formula 16. The reaction takes place at a temperature of about 0° C. to about 20° C. (room temperature) in the presence of a base, such as triethylamine, in an inert organic solvent such as dichloromethane.

EQ I depicts a method for preparing compounds of Formula 1 wherein X is —C(O)NR$^6$R$^7$.

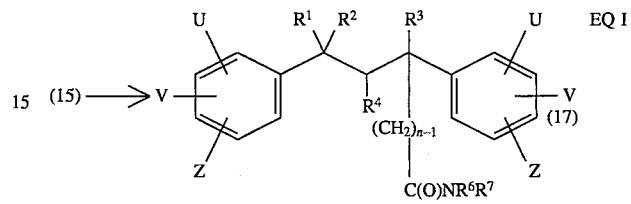

In EQ I, a compound of Formula 15 is reacted with an amine, HNR$^6$R$^7$, to produce a compound represented by Formula 17. The reaction takes place at a temperature of about 0° C. to about 20° C. (room temperature) in the presence of base such as triethylamine in an organic solvent such as dichlormethane or benzene.

EQ J depicts a method for preparing compounds of Formula 1 wherein X is —C(O)NR$^5$OH.

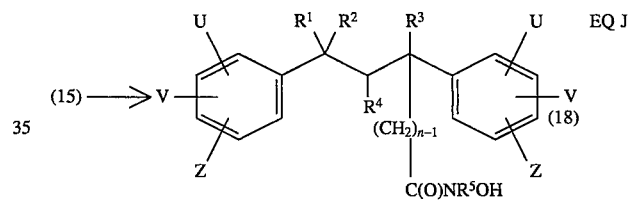

In EQ J, a compound of Formula 15 is reacted with HNR$^5$OH in an organic solvent. Examples of suitable organic solvents include benzene, THF, and the like. Preferably, THF is used. Most preferably an organic solvent/water combined solvent system is used. Preferably the combination is THF and water, 2:1 to 3:1 v/v. The reaction is usually carried out at a temperature of about 0° C. to about 20° C. (room temperature).

EQ K depicts the method of converting compounds of Formula 50 wherein R$^1$, R$^2$, R$^3$ and R$^4$ are as defined for Formula 1 and X is —OR$^{10}$, —CHO, —COOH, —COR$^{11}$, —OC(O)R$^9$ and —OC(O)NR$^5$R$^9$ to compounds of formula 51 and thereafter to compounds of formula 52 wherein U, V and Z are as defined for Formula 1.

Compounds of formula 52, where U V and Z are independently selected from —OH, —OC(O)R$^4$ and —OC(O)NR$^5$R$^9$ can be prepared from compounds of formula 50 wherein X can be —OR$^{10}$, —CHO, —COOH, —COR$^{11}$, —OC(O)R$^9$, and —OC(O)NR$^5$R$^9$.

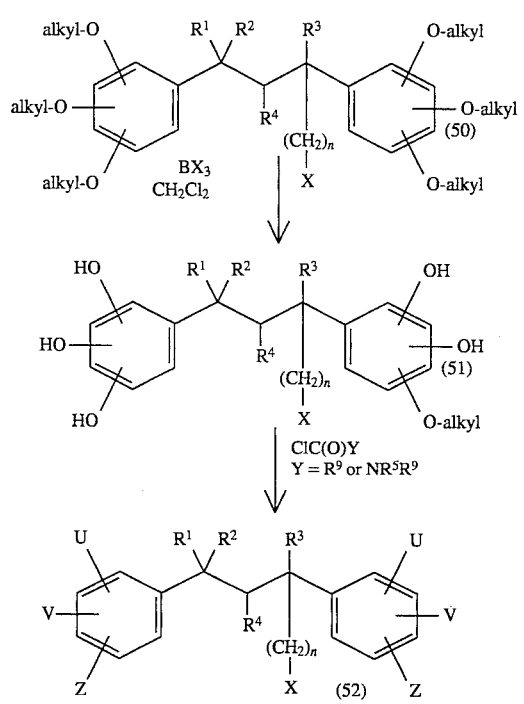

A compound of formula 50, where X=O alkyl, —OC(O)NR$^5$R$^9$, —C(O)R$^{11}$, —OC(O)R$^9$ is converted to a compound of formula 51 by Lewis acid in an inert organic solvent. Lewis acid is BBr$_3$, BCl$_3$ or AlCl$_3$. BBr$_3$ is preferred. The preferred inert organic solvent is CH$_2$Cl$_2$. The reaction is carried at about −78° C. to room temperature (about 20° C.). Compound 51 is allowed to react with an acid chloride such as ClC(O)Y, wherein Y=R$^9$ or —NR$^5$R$^9$, in the inert organic solvent in the presence of an organic base to produce a compound of formula 52. The organic base can be triethyl amine or pyridine. The organic solvent can be dichloromethane, pyridine or benzene. The reaction is carried out at temperatures of about −25° C. to 50° C.

EQs L, L', and M depict methods for preparing a compound of Formula 7 used as a starting material in EQ A.

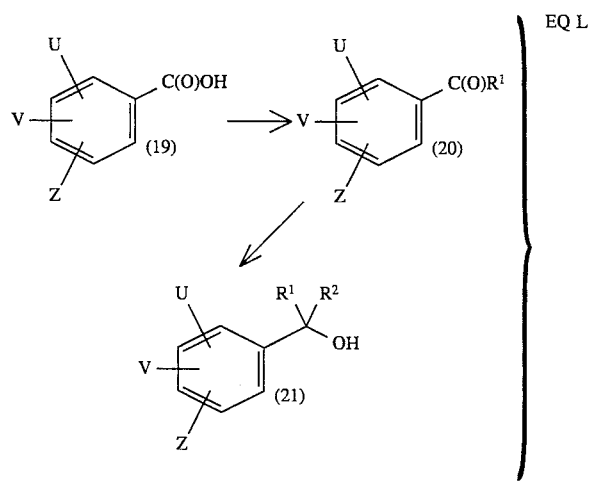

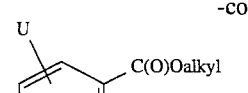

In EQ L, a compound of Formula 19 is reacted with R$^1$Li to produce a compound of Formula 20. This reaction takes place in an inert organic solvent such as ether or THF. The conversion of a compound of Formula 19 to a compound of Formula 20 is carried out at a temperature of about −78° C. to about 0° C.

Then, in EQ L, a compound of Formula 20 is reacted with R$^2$M to produce a compound of Formula 21 (intermediate for making a compound of Formula 7). In this reaction M can be Li or MgX, wherein X is Cl or Br. This reaction takes place in an organic solvent such as ether or THF at temperature of about −78° C. to about 20° C.

In EQ L', a compound of Formula 23 wherein R$^1$ and R$^2$ are the same is prepared. In this method a compound of Formula 22 is reacted with two equivalents of R$^1$MgX, wherein X is Cl or Br, to produce a compound of Formula 23. This reaction is carried out in an inert organic solvent such as THF, ether, and the like. Preferably ethyl ether is used. Also, this reaction may be carried out at a temperature of about −10° C. to about 50° C. with about 20° C. (room temperature) being preferred. The reactant R$^1$MgX is prepared by methods well known in the art.

In EQ M, a compound of Formula 21 (or Formula 23) is halogenated to produce a compound of Formula 7, wherein G is Br or Cl. The halogenation may be carried out using HX wherein X is a halo atom, with Br or Cl being preferred. This reaction takes place in an organic solvent such as CHCl$_3$, dichloromethane and the like. Preferably dichloromethane is used. This reaction is also carried out in the presence of a conventional inert drying agent such as anhydrous MgSO$_4$, and the like. The temperature at which this reaction is carried out is within a range of about −20° C. to about 10° C. with about 0° C. being preferred.

EQs N, 0 and P depict methods for preparing a compound of Formula 8, which is a starting material in EQ A.

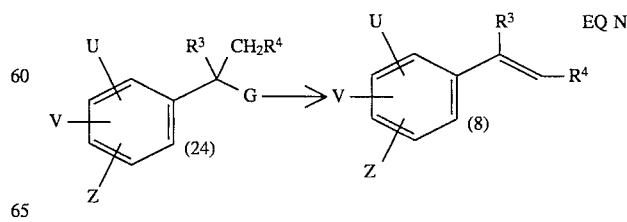

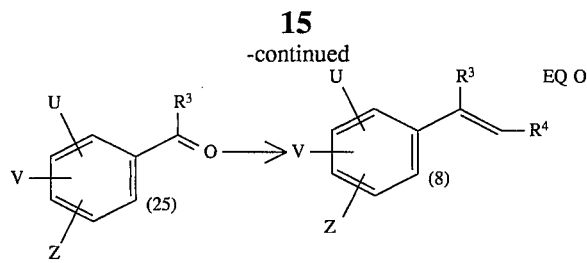

EQ O

Those skilled in the art will appreciate that the compound of Formula 24 in EQ N may be prepared in accordance with the methods of EQ L-M above except $R^3$ and —$CH_2R^4$ groups are used in place of $R^1$ and $R^2$ groups.

In EQ N, a compound of Formula 24 is reacted with a base to prepare a compound of Formula 8. Examples of bases include 1,8-Diazabicyclo[5.4.0]undec-7-ene [DBU], triethylamine, 4-dimethylaminopyridine [4-DMAP] and the like. The reaction takes place at a temperature within the range of about 0° C. to about 50° C. Alternatively, a compound of Formula 24 can be passed through basic alumina. This alternative method can be carried out at a temperature of about 20° C.

EQ O represents another method of preparing compounds of Formula 8. In this reaction a compound of Formula 25 is reacted with a Wittig reagent (Formula 29, EQ P below) to produce a compound of Formula 8. This reaction takes place in an organic solvent such as ether, DMSO, THF, and the like. Preferably THF is used. This reaction takes place at a temperature of about 0° C. to about 50° C.

The Wittig reagent, used in EQ O, may be prepared in accordance with well known procedures as exemplified in EQ P.

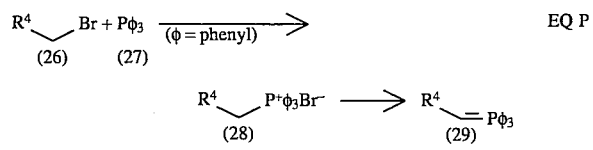

EQ P

In EQ P, a compound of Formula 28 is reacted with a base such as butyl lithium (BuLi) or NaH.

EQ Q(1) and Q(2) depict a method for preparing higher homologs at W of formula 1.

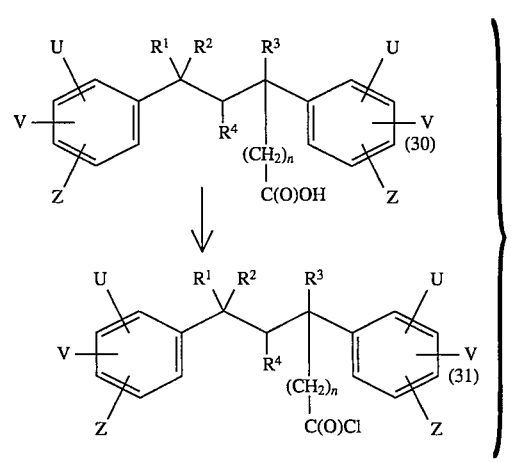

EQ Q(1)

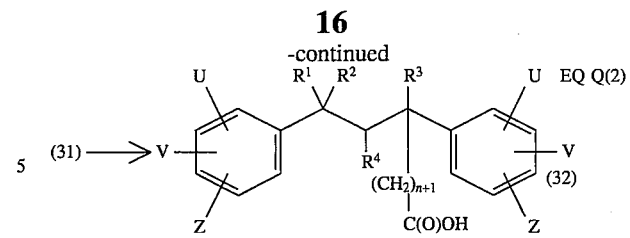

EQ Q(2)

The compound of Formula 30 is reacted with a chlorinating agent to form a compound of Formula 31. Examples of chlorinating agents include $(COCl)_2$ and $SOCl_2$.

To prepare the compound of Formula 32, the compound of Formula 31 is first reacted with diazomethane then reacted with water and $Ag_2O$. This reaction sequence is known as the Arndt-Estert Synthesis (for details see Arndt, F., Eistert, B., *Ber.*, 68, p. 200 (1935) or Aoyama, T., Shioiro, T., *Tet. Let.*, 21, P. 4461 (1980)).

The reaction sequences in EQ Q(1) and EQ Q(2) can be repeated as often as desired to produce the desired chain length.

EQs R(1)–(3) depict a method for preparing compounds of Formula 30.

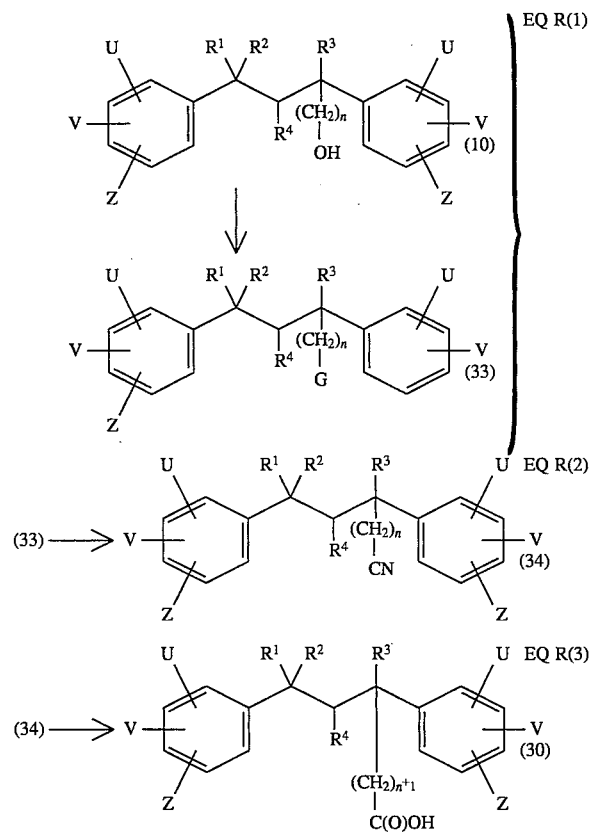

In EQ R(1), a compound of Formula 33 is prepared when a compound of Formula 10 is reacted with $G_2$ wherein G is a halogen atom, such as I or Br. The reaction takes place in the presence of $P\phi_3$ (wherein $\phi$ represents phenyl). The reaction is carried out at a temperature of about −10° C. to about 20° C.

The compound of Formula 33 is reacted with a cyanide, e.g. sodium cyanide, to form a compound of Formula 34. The reaction takes place in an organic solvent such as DME, DMSO or DMF, and the like. Preferably DMF is used. This reaction takes place at a temperature of about 0° C. to about 100° C. with about 20° C. to about 50° C. being preferred.

A compound of Formula 30 is then prepared from the compound of Formula 34 by hydrolysis using a strong base, such as NaOH, KOH and the like. The reaction may be carried out at a temperature of about 50° C. to about 100° C. in aqueous methanol or aqueous diethylene glycol.

EQ S(1) and EQ S(2) depict a method for preparing a higher homologue of Formula 1 compounds when X is $COR^{11}$ and $R^{11}$ is H.

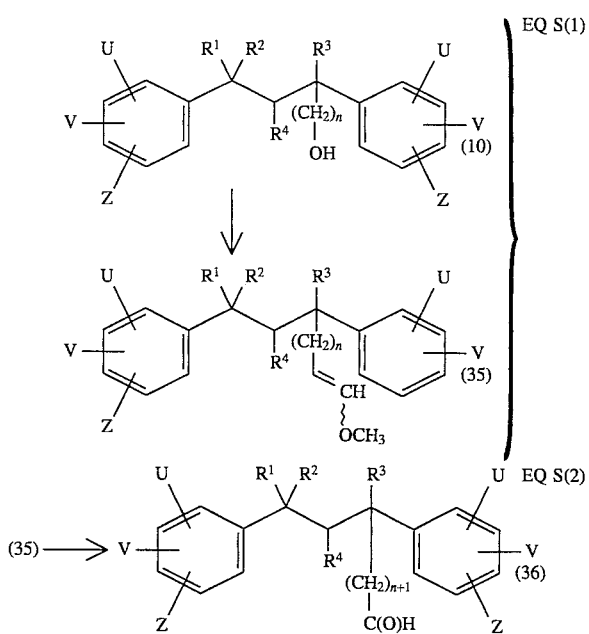

EQ S(1)

EQ S(2)

In EQ S(1), a compound of Formula 10 is reacted with a Wittig reagent

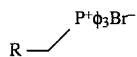

wherein R=—$OCH_3$, —O—ϕ—$CH_3$ or —Sϕ in the presence of a strong base to produce a compound of Formula 35. Examples of bases include $NaOC_2H_5$, t-BuOK and the like. The reaction is carried out at a temperature of about 0° C. to about 40° C. in an inert solvent such as ethanol or DME.

In EQ S(2), a compound of Formula 35 is reacted with an acid to produce a compound of Formula 36. Examples of suitable acids include $HClO_4$ or $H_2SO_4$ and the like. The reaction may be carried out at a temperature of about 0° C. to about 50° C. with about 20° C. (room temperature) being preferred.

EQ T(1) and EQ T(2) depict a method for producing lower homologous compounds, i.e. those which differ by a —$CH_2$—$CH_2$— group.

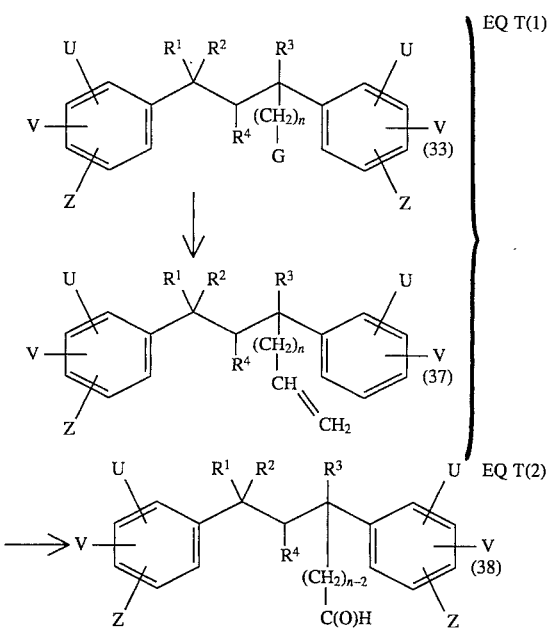

EQ T(1)

EQ T(2)

In EQ T(1), a compound of Formula 33 is reacted with a base to produce a compound of Formula 37. Examples of suitable bases include $NaNH_2$, DBU and the like. The reaction takes place in an inert organic solvent such as DMSO, THF, DME, and the like. The temperature, at which the reaction is carried out, is about 20° C. (room temperature) to about 100° C.

The compound of Formula 37 is then oxidized to the compound of Formula 38. The oxidation takes place using ozone ($O_3$) and an organic solvent such as dichloromethane. The reaction takes place at a temperature of about −78° C. to about 0° C.

EQ U(1) and U(2) depict another method for producing lower homologous compounds.

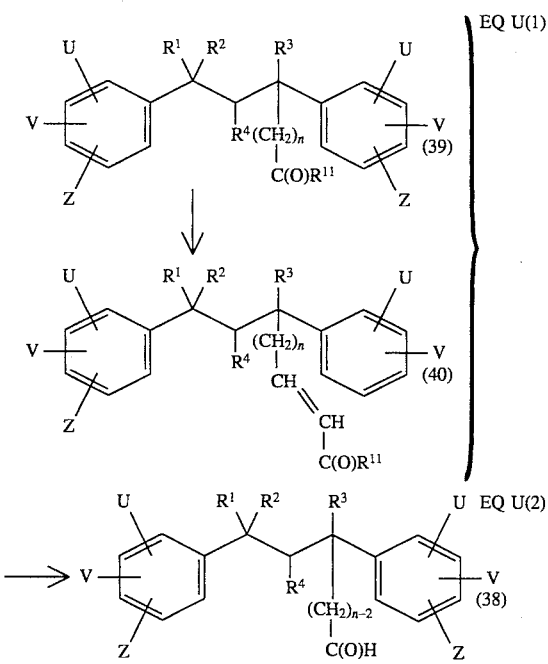

EQ U(1)

EQ U(2)

In EQ U(1), a compound of Formula 39 undergoes a series of reactions to produce a compound of Formula 40. In the reaction $R^{11}$ is H or an —$OR^5$ group in which $R^5$ is alkyl. The compound of Formula 39 is first reacted with a base, preferably lithium diisopropylamide (LDA). This reaction takes place in an organic solvent such as DME, ether or THF, and the like, preferably THF. Then, the resulting compound is reacted with φSeCl, φSCl, and the like, preferably φSeCl. The reactions take place at a temperature of about 0° C. to about 20° C. The resulting mixture is then treated with an oxidizing agent such as $H_2O_2$ to produce a compound of Formula 40. The oxidizing step takes place at a temperature of about 0° C. to about 50° C.

The compound of Formula 40 is oxidized to the compound of Formula 38 using $O_3$. The oxidation step takes place in an organic solvent such as dichloromethane, and the like. The reaction takes place at a temperature of about −78° C. to about 0° C.

In the above processes, it is desirable and sometimes necessary to protect the groups in column 1 of Table 1. Conventional protecting groups are operable. Preferred protected groups appear in column 2 of Table 1.

TABLE 1

PROTECTED GROUPS

| 1. GROUP TO BE PROTECTED | 2. PROTECTED GROUP |
|---|---|
| —COOH | —COOalkyl, —COObenzyl, —COOphenyl, (bicyclic orthoester with CH3) |
| \NH/ | \NCOalkyl, \NCObenzyl, \NCOphenyl |
| \CO/ | (cyclic acetals) |
| —OH | —O-(tetrahydropyranyl), —OCH2phenyl, —OCH3, OSi(CH3)2(t-Bu) |
| —NHR, wherein R is any substituent on an amino group within the scope of the claims | —N(R)-(tetrahydropyranyl), —NRCOCH3, —NRCH2phenyl |

TABLE 1-continued

PROTECTED GROUPS

| 1. GROUP TO BE PROTECTED | 2. PROTECTED GROUP |
|---|---|
| —NH2 | —N(succinimide), —NH—C(O)—O(t-Bu) |

Of course other protecting groups well known in the art may be used. After the reaction or reactions, the protecting groups may be removed by standard procedures well known in the art Representative compounds of Formula 1 include Formulas 41–46:

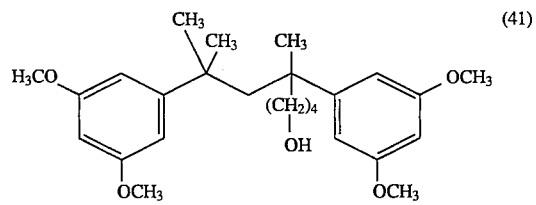

(41)

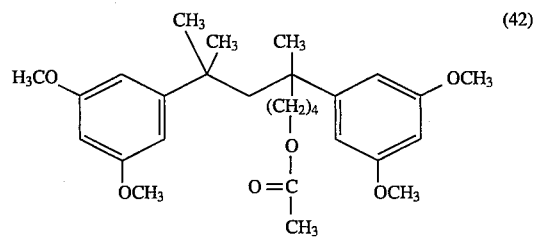

(42)

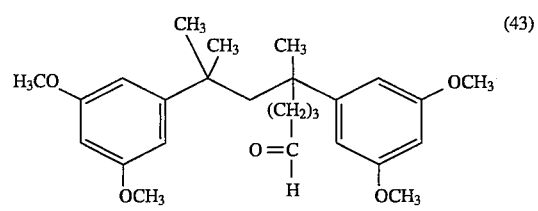

(43)

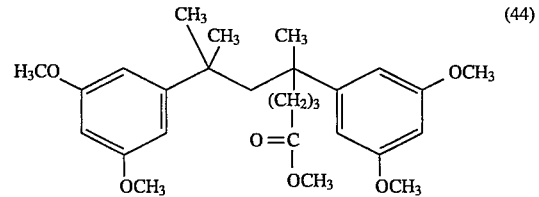

(44)

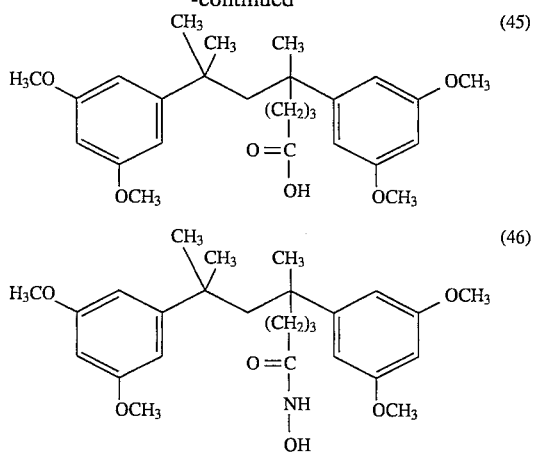

The 5-LO inhibitory activity of the compounds of this invention may be demonstrated by the procedures described below.

5-Lipoxygenase Assay with Human Neutrophils

Human polymorphonuclear leukocytes (neutrophils) were obtained from normal healthy volunteers by venipuncture and collected with heparin anticoagulant. Neutrophils were isolated by Dextran/Ficol sedimentation as described (Billah et al., J. Biol. Chem. 260, 6899–6906 (1985)). In brief, 30 ml of blood was mixed with 5 ml of dextran (Sigma) solution and kept at 37 C for 30 min. The upper white cell-rich layer was removed and 10 ml was layered on 9 ml of Ficol-Pague solution (Pharmacia) and centrifuged at 280×g for 10 min. at 5° C. The supernatant was removed and the neutrophil pellet was resuspended in HEPES buffer containing 25 mM N-2-hydroxyethylpiperazine-$N^1$-2-ethanesulfonic acid (HEPES), 125 mM NaCl, 2.5 mM KCl, 0.7 mM $MgCl_2$, 0.5 mM and 10 mM glucose at pH 7.4. The red cells in the suspension were lysed by hypotonic shock. The neutrophils were washed by centrifugation in HEPES buffer two times and finally resuspended at a concentration of $20\times10^6$ cells/ml in the presence of 1 mM $CaCl_2$.

Neutrophils (0.2 ml of suspension) were preincubated with dimethylsulfonxide (DMSO) vehicle with or without test compound (1 µl) for 4 minutes then incubated for 5 minutes with [$^{14}$C] arachidonic acid (Amersham, 59 Ci/mole) at a 9 µM final concentration, and the calcium ionophore A23187 (Calbiochem) at a 1 µM final concentration. These stimulants were added in 10 µl of water:ethanol (9:1). The reaction was stopped by addition of methanol (0.4 ml), and cellular debris was removed by centrifugation. Aliquots (100 ul) of the incubations were run on a Waters two pump HPLC system fitted with a DuPont Zorbax ODS, 5µ, 4×80 cm Reliance Cartridge column and C18 "Guard Pak". The column was initially eluted at 2 ml/min with 80% of the mixture water:methanol:acetic acid (46:54:0.08) containing 1 mM EDTA adjusted to pH 6.0 with ammonium hydroxide (Pump A) and 20% methanol (Pump B). At 10 minutes, a linear gradient to reach 100% methanol (Pump B) at 27 minutes was established. Between 27 and 28 minutes, methanol was exchanged for the initial eluting solvent and by 35 minutes the column had been reequilibrated for the next sample. The effluent was analyzed by a continuous flow radioactivity monitor (model ROMONA-D) interfaced with a Hewlett Packard Lab Automation System for quantitation of radioactive products. These were predominantly leukotriene $B_4$ ($LTB_4$) which eluted at 7 minutes, and 5-hydroxyeicosatetraenoic acid (5-HETE) which eluted at 20 minutes.

The results with and without test compound were used to calculate percent inhibition of $LTB_4$ and 5-HETE production for representative compounds of the invention as shown in Table 2 below.

TABLE 2

| | 5-LO INHIBITION | | |
|---|---|---|---|
| | | % INHIBITION | |
| FORMULA | DOSE (µM) | 5-HETE | $LTB_4$ |
| 41 | 15 | 99 | 97 |
| 42 | 15 | 95 | 100 |
| 43 | 15 | 97 | 97 |
| 44 | 15 | 98 | 100 |
| 45 | 15 | 33 | 14 |
| 46 | 15 | 99 | 96 |
| 46 | 5 | 63 | — |

The results in Table 2 demonstrate that the compounds of this invention inhibit 5-LO activity as evidenced by their inhibition of 5-HETE and $LTB_4$. They also demonstrate that certain compounds due to their substituent groups may have different potencies.

The compounds of this invention, as stated above, are useful in the treatment of hyperproliferative skin disease. This may be demonstrated by their 5-lipoxygenase inhibitory activity as discussed above or by the Arachidonic Acid Mouse Ear Test as described below.

Arachidonic Acid Mouse Ear Test

Materials and Methods

Charles River, female, CD, (SD) BR mice, 6 weeks old, are caged 8/group and allowed to acclimate 1–3 weeks prior to use.

Arachidonic acid (AA) is dissolved in reagent grade acetone (2 mg/0.01 ml) and stored at −20° C. for a maximum of 1 week prior to use. Inflammatory reactions are induced by applying 10 µl of AA to both surfaces of one ear (4 gm total).

Test drugs are dissolved in either reagent grade acetone or aqueous ethanol (only if insoluble in acetone) at the same doses selected by Opas et al., Fed. Proc. 43, Abstract 2983, p. 1927 (1984) and Young et al., J. Invest. Dermatol. 82, pp. 367–371 (1984). These doses are employed to ensure maximum responses and to overcome any difference in topical absorption which could occur with any drug applied in an aqueous ethanol vehicle. The test drug is applied 30 minutes prior to challenge with AA.

The severity of the inflammation is measured as a function of increased ear weight. A 6 mm punch biopsy is removed 1 hour after AA challenge and weighed to the nearest 0.1 mg. Mean±standard error and all possible comparisons are made via Duncan's Multiple Range Statistic.

The results of this test are given in Table 3 below.

TABLE 3

| MOUSE EAR ASSAY | | |
|---|---|---|
| FORMULA | DOSE (MG/EAR) | % INHIBITION |
| 41 | 1.0 | 72 |
| 42 | 0.5 | 40 |

The results in Table 3 show that the compounds of this invention demonstrate anti-inflammatory activity made apparent by the low percent increase in ear weight when applied topically.

The compounds of this invention can be used to treat allergies in mammals (e.g., humans) and a preferred use is for treating allergic chronic obstructive lung disease (sometimes referred to as COPD or chronic obstructive pulmonary disease). Chronic obstructive lung disease as used herein means disease conditions in which the passage of air into and out of the lungs is obstructed or diminished such as is the case in asthma, allergic or seasonal rhinitis, and/or bronchitis and the like.

The compounds of this invention inhibit 5-lipoxygenase (5-LO) activity, which inhibitory activity has been associated with antiallergic, antiinflammatory and antihyperproliferative activity. The compounds of the invention are thus useful for the treatment of allergic diseases as discussed above, inflammatory diseases and hyperproliferative skin diseases.

The inflammatory diseases which may be treated include arthritis, bursitis, tendonitis, gout and inflammatory bowel disease.

"Hyperproliferative skin disease" means any condition a symptom of which is accelerated skin cell production, flaking, scales or papular lesions. Examples of hyperproliferative skin diseases include for example, psoriasis, lichenified eczema, dandruff and the like.

The compounds of this invention can be administered in any number of conventional dosage forms, e.g., topical, oral, parenteral, rectal, transdermal, inhalation and the like. Oral or rectal dosage forms include capsules, tablets, pills, powders, cachets and suppositories. Liquid oral dosage forms include solutions and suspensions. Parenteral preparations include sterile solutions and suspensions. Inhalation administration can be in the form of a nasal or oral spray, or by insufflation. Topical dosage forms can be creams, ointments, lotions, transdermal devices (e.g., of the conventional patch or matrix type) and the like and are preferred for treating hyperproliferative skin diseases.

The formulations and pharmaceutical compositions contemplated by the above dosage forms can be prepared with conventional pharmaceutically acceptable excipients and additives, using conventional techniques. Such pharmaceutically acceptable excipients and additives are intended to include carriers, binders, flavorings, buffers, thickeners, color agents, stabilizing agents, emulsifying agents, dispersing agents, suspending agents, perfumes, preservatives lubricants, etc.

Suitable pharmaceutical acceptable solid carriers are magnesium carbonate, magnesium stearate, talc, sugar, lactose, pectin, dextrin, starch, gelatin, tragacanth, methylcellulose, sodium carboxymethylcellulose, low melting waxes, cocoa butter and the like. Capsules can be made wherein the active compound is inserted into pharmaceutically acceptable capsules as a carrier. The active compounds of this invention can be mixed with pharmaceutically acceptable excipients or be used in finely divided powder form without excipients for inclusion into the capsules. Similarly, cachets are included.

Liquid form preparations include solutions, suspensions and emulsions. As an example may be mentioned water or water-propylene glycol solutions for parenteral injection. Liquid preparations can also be formulated in solution in polyethylene glycol and/or propylene glycol, which may contain water. Aqueous solutions suitable for oral use can be prepared by adding the active component in water and adding suitable colorants, flavors, stabilizing, sweetening, solubilizing and thickening agents as desired. Aqueous suspensions suitable for oral use can be made by dispersing the active component in finely divided form in water with viscous material, i.e., pharmaceutically acceptable natural or synthetic gums, resins, methylcellulose, sodium carboxymethylcellulose and other well-known suspending agents.

Formulations for topical application, e.g., for use in treating hyperproliferative skin diseases, may include the above liquid forms, as well as creams, aerosols, sprays, dusts, powders, lotions and ointments which are prepared by combining an active ingredient according to this invention with conventional pharmaceutical acceptable diluents and carriers commonly used in topical dry, liquid, cream and aerosol formulations. Ointment and creams may, for example, be formulated with an aqueous or oily base with the addition of suitable thickening and/or gelling agents. Such bases may, thus, for example, include water and/or an oil such as liquid paraffin or a vegetable oil such as peanut oil or castor oil. Thickening agents which may be used according to the nature of the base include soft paraffin, aluminum stearate, cetostearyl alcohol, propylene glycol, polyethylene glycols, woolfat, hydrogenated lanolin, beeswax, etc.

Lotions may be formulations with an aqueous or oil base and will, in general, also include one or more of pharmaceutically acceptable stabilizing agents, emulsifying agents, dispersing agents, suspending agents, thickening agents, coloring agents, perfumes and the like.

Powders may be formed with the aid of any suitable pharmaceutically acceptable powder base, e.g., talc, lactose, starch, etc. Drops may be formulated with an aqueous base or non-aqueous base also comprising one or more pharmaceutically acceptable dispersing agents, suspending agents, solubilizing agents, etc.

The topical pharmaceutical compositions may also include one or more preservatives or bacteriostatic agents, e.g., methyl hydroxybenzoate, propyl hydroxybenzoate, chlorocresol, benzalkonium chlorides, etc.

The topical pharmaceutical compositions may also contain an active compound of this invention in combination with other active ingredients such as antimicrobial agents, particularly antibiotics, anesthetics, analgesics and antipruritic agents.

Also included are solid form preparations which are intended to be converted, shortly before use, to liquid form preparations for either oral or parenteral administration. Such liquid forms include solutions, suspensions and emulsions. These particular solid form preparations are most conveniently provided in unit dose form and as such are used to provide a single liquid dosage unit. Alternatively, sufficient solid may be provided so that after conversion to liquid form, multiple individual liquid doses may be obtained by measuring predetermined volumes of the liquid form preparation as with a syringe, teaspoon or other volumetric container. When multiple liquid doses are so prepared, it is preferred to maintain the unused portion of said liquid doses under conditions which retard possible decomposition. The solid form preparations intended to be converted to liquid form may contain, in addition to the active material, pharmaceutically acceptable flavorants, colorants, stabilizers, buffers, artificial and natural sweeteners, dispersants, thickeners, solubilizing agents and the like. The solvent utilized for preparing the liquid form preparation may be water, isotonic water, ethanol, glycerine, propylene glycol and the like as well as mixtures thereof. Naturally, the solvent utilized will be chosen with regard to the route of administration, for example, liquid preparations containing large amounts of ethanol are not suitable for parenteral use.

The compounds of this invention may also be deliverable transdermally for systemic distribution. The transdermal compositions can take the form of creams, lotions and/or emulsions and can be included in a transdermal patch of the matrix or reservoir type as are conventional in the art for this purpose.

The compounds of this invention may be administered by any conventional mode of administration, by employing an anti-allergic, anti-inflammatory or antihyperproliferative effective amount of a compound of this invention for such mode. The dosages may be varied depending upon the requirements of the patient in the judgment of the attending clinician, the severity of the condition being treated and the particular compound being employed. Determination of the proper dosage for a particular situation is within the skill of the art. Treatment can be initiated with smaller dosages which are less than the optimum dose of the compound. Thereafter, the dosage should be increased by small increments until the optimum effect under the circumstances is reached. For convenience, the total daily dosage may be divided and administered in portions during the day if desired.

Thus, depending on the mode, dosages of from about 0.1 to about 100 mg/kg of body weight per day may be administered. For example, when administered orally they exhibit antiallergy activity at doses of from about 0.5 to about 25 mg/kg of body weight and preferably about 0.5 to about 10 mg/kg; when administered parenterally, e.g., intravenously, the compounds exhibit antiallergy activity at dosages of from about 0.1 to about 5 mg/kg body weight and preferably about 0.1 to about 2.5 mg/kg, and when administered by inhalation (aerosol or nebulizer) the compounds exhibit antiallergy activity at dosages of about 0.1 to about 5 mg per puff, and one to four puffs may be taken every 4 hours. The dosage to be administered and the route of administration depends upon the particular compound used, the age and general health of the patient and the severity of the allergic condition. Thus, the dose ultimately decided upon must be left to the judgment of a trained health-care practitioner.

The compounds of this invention can be administered by any conventional mode of administration, to obtain the anti-inflammatory activity by employing an anti-inflammatory effective amount of a compound of this invention. The compounds of this invention, as an anti-inflammatory agent, may be administered at doses of about 0.1 to about 100 mg/kg of body weight per day, and preferably about 5 to about 50 mg/kg per day. Preferably the total dosages are administered in 2 to 4 divided doses per day. For example, an oral dosage range of from about 5 mg/kg of body weight per day to about 50 mg/kg of body weight per day in divided doses taken at about 4 hour intervals may be used.

When administered for the treatment of hyperproliferative skin disease, the compounds of this invention may be administered topically, orally, rectally or parenterally, with topically preferred. When administered topically, the amount of compound administered varies widely with the amount of skin being treated, as well as with the concentration of active ingredient applied to the affected area. Preferably, topical compositions contain from about 0.10 to about 10 percent by weight of the active ingredient and are applied as needed according to the judgment of the attending clinician. When administered orally, the compounds of formula I are effective for the treatment of hyperproliferative skin disease at daily doses ranging from about 0.1 mg/kg to about 100 mg/kg of body weight, preferably from about 5 mg/kg to about 50 mg/kg, which may be administered in divided doses. When administered rectally, the compounds of this invention may be administered in daily doses ranging from about 0.1 mg/kg to about 100 mg/kg. When administered parenterally, the compounds of this invention are effective for the treatment of hyperproliferative skin disease in daily doses ranging from about 0.1 mg/kg body weight to about 10 mg/kg body weight which may be administered in divided doses.

As a result of the administration of a compound of this invention, a remission of the symptoms of the psoriatic patient, in most cases, can be expected. Thus, one affected by psoriasis can expect a decrease in scaling, erythema, size of the plaques, pruritus and other symptoms associated with psoriasis. The dosage of medicament and the length of time required for successfully treating each individual psoriatic patient may vary, but those skilled in the art of medicine will be able to recognize these variations and adjust the course of therapy accordingly.

The following formulations exemplify some of the dosage forms of the compositions of this invention. In each, the term "active compound" refers to compound 41. However, this compound may be replaced by equally effective amounts of other compounds, e.g. those of formulas 42, 43, 44, 45 or 46 of this invention.

EXAMPLE A
Tablets

| No. | Ingredient | mg/tablet | mg/tablet |
|---|---|---|---|
| 1. | Active compound | 100 | 500 |
| 2. | Lactose USP | 122 | 113 |
| 3. | Corn Starch, Food Grade, as a 10% paste in Purified Water | 30 | 40 |
| 4. | Corn Starch, Food Grade | 45 | 40 |
| 5. | Magnesium Stearate | 3 | 7 |
|  | Total | 300 | 700 |

Method of Manufacture

Mix Item Nos. 1 and 2 in a suitable mixer for 10–15 minutes. Granulate the mixture with Item No. 3. Mill the damp granules through a coarse screen (e.g., ¼", 0.63 cm) if necessary. Dry the damp granules. Screen the dried granules if necessary and mix with Item No. 4 and mix for 10–15 minutes. Add Item No. 5 and mix for 1–3 minutes. Compress the mixture to appropriate size and weigh on a suitable tablet machine.

EXAMPLE B
Capsules

| No. | Ingredient | mg/capsule | mg/capsule |
|---|---|---|---|
| 1. | Active compound | 100 | 500 |
| 2. | Lactose USP | 106 | 123 |
| 3. | Corn Starch, Food Grade | 40 | 70 |
| 4. | Magnesium Stearate NF | 4 | 7 |
|  | Total | 250 | 700 |

Method of Manufacture

Mix Item Nos. 1, 2 and 3 in a suitable blender for 10–15 minutes. Add Item No. 4 and mix for 1–3 minutes. Fill the mixture into suitable two-piece hard gelatin capsules on a suitable encapsulating machine.

| EXAMPLE C Parenteral Preparation | | |
|---|---|---|
| Ingredient | mg/vial | mg/vial |
| Active Compound Sterile Powder | 100 | 500 |

For reconstitution add sterile water for injection or bacteriostatic water for injection.

| EXAMPLE D Injectable | |
|---|---|
| Ingredient | mg/vial |
| Active Compound | 100 |
| Methyl p-hydroxybenzoate | 1.8 |
| Propyl p-hydroxybenzoate | 0.2 |
| Sodium Bisulfite | 3.2 |
| Disodium Edetate | 0.1 |
| Sodium Sulfate | 2.6 |
| Water for Injection q.s. ad | 1.0 ml |

Method of Manufacture (for 1000 Vials)

1. Dissolve p-hydroxybenzoate compounds in a portion (85% of the final volume) of the water for injection at 65°–70° C.

2. Cool to 25°–35° C. Charge and dissolve the sodium bisulfite, disodium edetate and sodium sulfate.

3. Charge and dissolve active compound.

4. Bring the solution to final volume by added water for injection.

5. Filter the solution through 0.22 membrane and fill into appropriate containers.

6. Finally sterilize the units by autoclaving.

| EXAMPLE E Nasal Spray | |
|---|---|
| Ingredient | mg/ml |
| Active Compound | 10.0 |
| Phenyl Mercuric Acetate | 0.02 |
| Aminoacetic Acid USP | 3.7 |
| Sorbitol Solution, USP | 57.0 |
| Benzalkonium Chloride Solution | 0.2 |
| Sodium Hydroxide 1N Solution to adjust pH | — |
| Water Purified USP to make | 1.0 ml |

The following formulations exemplify some of the dosage forms in which the anti-psoriatic agents of the invention may be employed.

| EXAMPLE F Ointment | |
|---|---|
| Ingredient | mg/g |
| Active Compound | 1.0–20.0 |
| Benzyl Alcohol, NF | 20.0 |
| Mineral Oil, USP | 50.0 |
| White Petrolatum, USP to make | 1.0 g |

Method of Manufacture

Disperse active compound in a portion of the mineral oil. Mix and heat to 65° C., a weighed quantity of white petrolatum, the remaining mineral oil and benzyl alcohol, and cool to 50°–55° C. with stirring. Add the dispersed active compound to the above mixture with stirring. Cool to room temperature.

| EXAMPLE G Cream | |
|---|---|
| Ingredient | mg/g |
| Active Compound | 1.0–20.0 |
| Stearic Acid, USP | 60.0 |
| Glyceryl Monostearate | 100.0 |
| Propylene Glycol, USP | 50.0 |
| Polyethylene Sorbitan Monopalmitate | 50.0 |
| Sorbitol Solution, USP | 30.0 |
| Benzyl Alcohol, NF | 10.0 |
| Purified Water, USP to make | 1.0 g |

Method of Manufacture

Heat the stearic acid, glyceryl monostearate and polyethylene sorbitan monopalmitate to 70° C. In a separate vessel, dissolve sorbital solution, benzyl alcohol, water, and half quantity of propylene glycol and heat to 70° C. Add the aqueous phase to oil phase with high speed stirring. Dissolve the active compound in remaining quantity of propylene glycol and add to the above emulsion when the temperature of emulsion is 37°–40° C. Mix uniformly with stirring and cool to room temperature.

| EXAMPLE H Gel | |
|---|---|
| Ingredient | mg/g |
| Active Compound | 1.0–20.0 |
| Propylene Glycol, USP | 300.0 |
| Butyrated Hydroxytoluene | 5.0 |
| Carbomer 940 | 5.0 |
| Sodium Hydroxide (added as a 1% w/w solution in propylene glycol) | 0.7 |
| Polyethylene Glycol 400, USP | 669.3–688 |

Method of Manufacture

Prepare a 1% solution of the sodium hydroxide in propylene glycol. Add approximately one-half the remaining propylene glycol and the polyethylene glycol 400 to a suitable vessel and mix. Dissolve the butylated hydroxytoluene in this mixture. Disperse the carbomer 940 in the above mixture with vigorous agitation. Add the solution of sodium hydroxide with high speed agitation to bring pH up to 7 and mix until a thick gel forms. Dissolve the active compound in the remaining propylene glycol and add to the gel slowly as the gel is continuously mixed.

| EXAMPLE I Lotion | |
|---|---|
| Ingredient | mg/g |
| Active Compound | 1.0–20.0 |
| Carbomer 940 | 3.0 |
| Sodium hydroxide (charged as 4% w/w | 0.05 |

EXAMPLE I
Lotion

| Ingredient | mg/g |
|---|---|
| aqueous solution) | |
| Isopropyl Alcohol | 40.00 |
| Purified Water, USP to make | 1.0 g |

Method of Manufacture

Prepare a 4% solution of sodium hydroxide in water. Heat the purified water to 60° C. Add carbomer 940 and mix at high speed until dispersed. Cool the above mixture to room temperature and slowly charge sodium hydroxide solution until uniform. Add 80% of isopropyl alcohol to the above with mixing. Dissolve the active compound in remaining isopropyl alcohol. Add this to the mixture with stirring. Adjust pH to 5.0 to 5.5 with sodium hydroxide, if necessary.

EXAMPLE J
Topical Aerosol

| Ingredient | mg/g |
|---|---|
| Active Compound | 1.0–20.0 |
| Caprylic/Capric Triglyceride | 50.00 |
| Mineral Oil | 20.00 |
| Denatured Alcohol | 150.00 |
| Hydrocarbon Aerosol Propellant q.s. ad. | 1.0 g |

Method of Manufacture

Add and mix the caprylic/capric triglyceride mineral oil and specially denatured alcohol in a suitable compounding tank, Add the active compound and continue mixing until the active compound is dissolved or dispersed uniformly. Fill the concentrate into cans and then fill the required amount of hydrocarbon aerosol propellant.

The following examples illustrate the preparation of compounds of this invention.

In the Examples which follow, the abbreviations used are:
tlc—thin layer chromatography
Ac₂O—acetic anhydride
EtOAc—ethyl acetate
PDC—pyridinium dichromate
Et₂O—ether (ethyl ether)
P.E.—petroleum ether
DMF—dimethyl formamide
AcOH—acetic acid
EtOH—ethyl alcohol (ethanol)
Et₃N—triethyl amine.

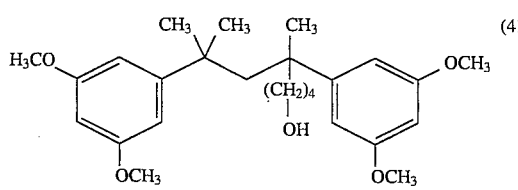
(41)

(1A) Preparation of reactants—Formula A

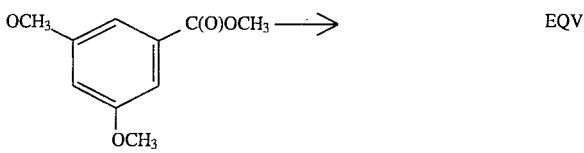 EQV

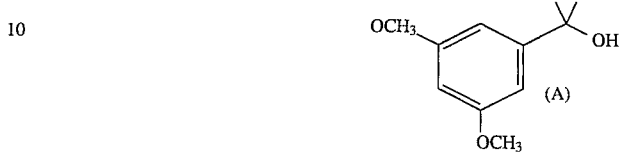
(A)

To a flask equipped with a rubber septum, a condenser with N₂ inlet and a dropping funnel was introduced 109 ml of 3.0N methyl magnesium bromide by syringe. A solution of 30 g of methyl 3,5-dimethoxybenzoate in 80 ml of anhydrous ether was added to the stirred Grignard solution through the dropping funnel over 40 minutes under N₂ at room temperature. During the addition the reaction mixture started to reflux gently. After the addition the resulting mixture was stirred for another hour. It was then cooled to −10° C. and quenched slowly by adding saturated aqueous NH₄Cl solution. The organic layer was separated. The aqueous layer was extracted with ethyl ether and the combined organic layers were washed with brine, dried over anhydrous MgSO₄ and concentrated to give 30.50 g of oil which crystallized on standing. The product was purified by column chromatography on SiO₂ (eluting solvents 2:1 CH₂Cl₂/Hexane, then CH₂Cl₂, and then gradient up to 15% ether in CH₂Cl₂) to give 28.8 g (96% yield), m.p. 52.5°–54° C., of pure product (Formula A, EQ V).

(1B) Preparation of reactants—Formula B, EQ W

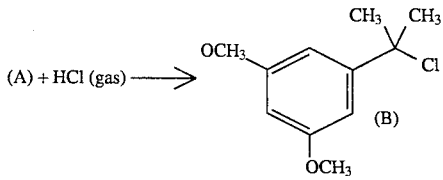 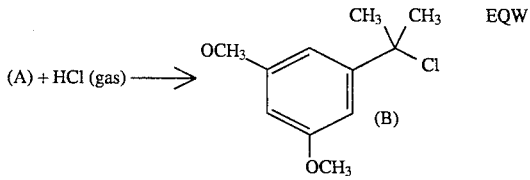 EQW
(B)

Into a flask equipped with a nitrogen inlet, a rubber septum, and a drying tube was introduced a solution of 30 g of the compound of Formula A (EQ V) in 150 ml of anhydrous CH₂Cl₂ and 19.6 g of anhydrous MgSO₄ was added. The stirred mixture was cooled in an ice water bath, then dry HCl gas was bubbled in for 55 minutes at 0° C. (until HCl was escaping through the drying tube). The reaction mixture was filtered and the filtrate was concentrated in vacuum to give an oil which solidified at −78° C. to give the compound of Formula B above. The product, Formula B, was thermally unstable and moisture sensitive and was maintained under nitrogen and at low temperature.

(1C) Preparation of reactants - Formula C, EQX

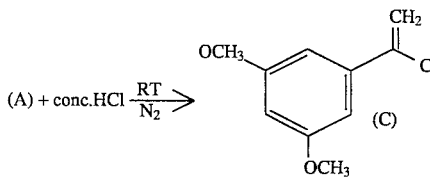 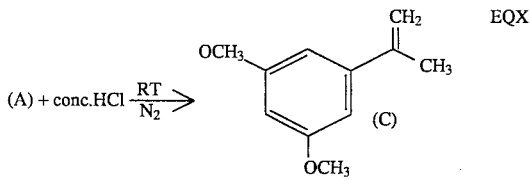 EQX
(C)

Conc. HCl (8.8 ml) was added to 7.02 g of the compound of Formula A (EQ V), and the mixture was stirred at room temperature (RT) for 30 minutes under N₂. The mixture was then extracted with 4×15 ml of anhydrous ether. The combined ether extracts were concentrated using a rotor evaporator. The residue (light yellow oil) was passed through a column of basic $Al_2O_3$ (eluting solvent: $CH_2Cl_2$) to give 4.57 g of olefin product Formula C (72% yield).

(1D) Preparation of compound of Formula 41 from compounds of Formulas B and C $K + MgCl_2 + KI \longrightarrow$ MIXTURE  (EQY(1))

MIXTURE + (A) + (B) $\longrightarrow$  (EQY(2))

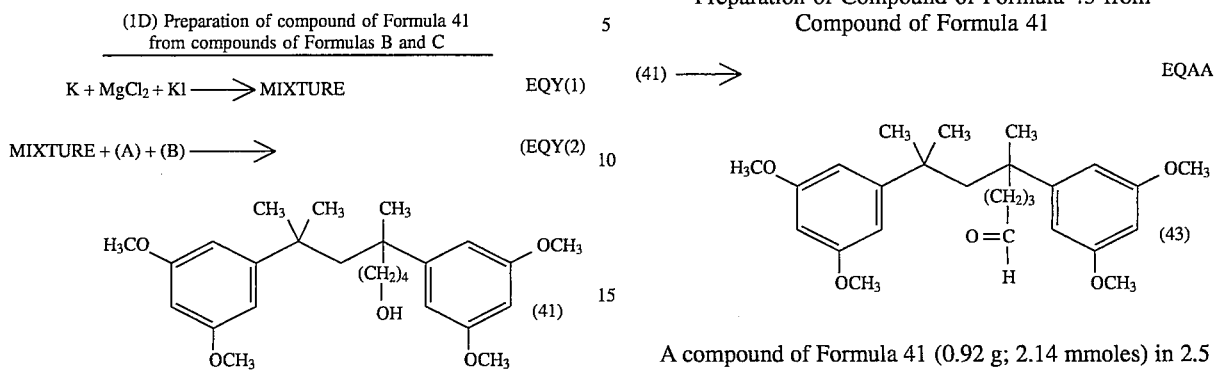

To a mixture of 0.546 g of potassium in 19 ml of anhydrous THF (tetrahydrofuran) was added 0.729 g of magnesium chloride and 1.287 g of potassium iodide. The resulting mixture was refluxed with vigorous stirring for 3 hours under nitrogen. After cooling to room temperature, a solution of 0.566 g of a compound of Formula B and 0.47 g of compound of Formula C in 1.25 ml of anhydrous THF was added dropwise to the mixture. This reaction mixture was stirred at room temperature for ½ hour, then it was quenched by adding saturated aqueous $NH_4Cl$ solution. Two layers were separated and the aqueous layer was extracted with ethyl ether. The combined organic extracts were washed with brine, dried over anhydrous $MgSO_4$ and then concentrated to give 2.48 g of oil residue. The oil residue was purified by chromatography on $SiO_2$ (20% ethyl acetate in hexane) to give 0.615 g (56% yield) of the product of Formula 41. MS(CI) m/e 431 (M+1)

EXAMPLE 2

Preparation of Compound of Formula 42 from Compound of Formula 41

(41) $\longrightarrow$  EQZ

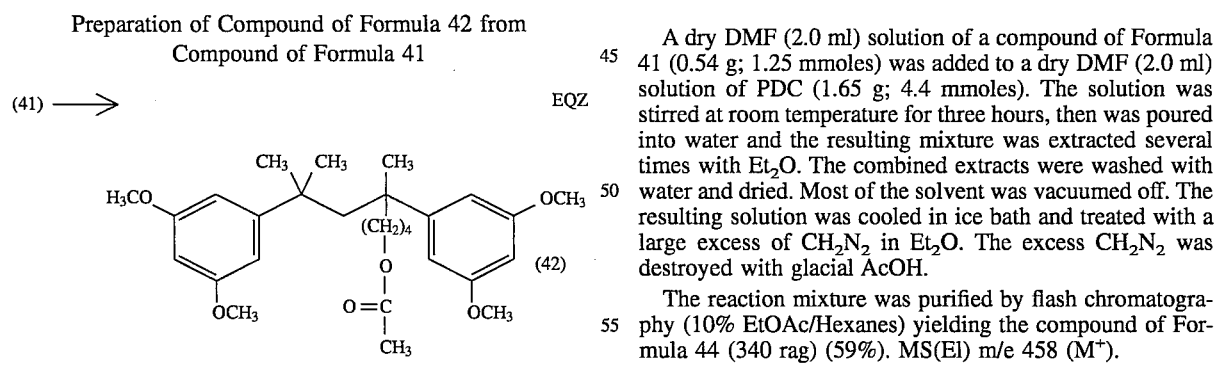

The compound of Formula 41 (0.5 g) was stirred at room temperature in 3 ml of pyridine and 1.0 ml of $Ac_2O$. The solution was stirred at room temperature for 16 hours, then the solvents were removed using high vacuum. The residue was treated with water and extracted with $CH_2Cl_2$. The combined extracts were washed with water and dried ($Na_2SO_4$). The reaction mixture was purified by flash chromatography (15% EtOAc/Hexanes) yielding the compound of Formula 42 (93%). MS(EI) m/e 472 ($M^+$).

EXAMPLE 3

Preparation of Compound of Formula 43 from Compound of Formula 41

(41) $\longrightarrow$  EQAA

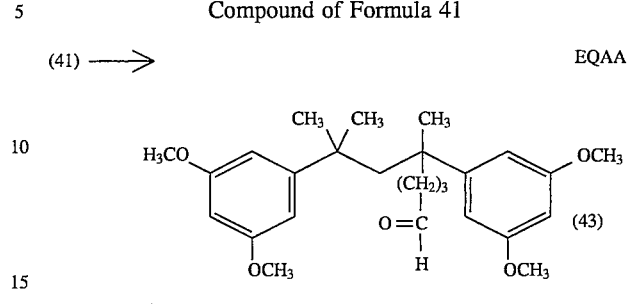

A compound of Formula 41 (0.92 g; 2.14 mmoles) in 2.5 ml of dry $CH_2Cl_2$ was added to a suspension of 1.21 g (3.21 mmoles) of PDC in dry $CH_2Cl_2$ (1.0 ml). The mixture was stirred at room temperature under $N_2$ for 16 hours. The mixture was diluted with $Et_2O$ and the solid is filtered through "Celite". The reaction mixture was purified by flash chromatography (15% EtOAc/petroleum ether) yielding the compound of Formula 43 (45%). MS(EI) m/e 428 ($M^+$).

EXAMPLE 4

Preparation of Compound of Formula 44 from Compound of Formula 41

(41) $\longrightarrow$  EQBB

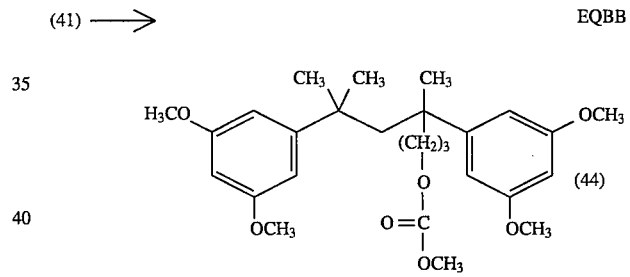

A dry DMF (2.0 ml) solution of a compound of Formula 41 (0.54 g; 1.25 mmoles) was added to a dry DMF (2.0 ml) solution of PDC (1.65 g; 4.4 mmoles). The solution was stirred at room temperature for three hours, then was poured into water and the resulting mixture was extracted several times with $Et_2O$. The combined extracts were washed with water and dried. Most of the solvent was vacuumed off. The resulting solution was cooled in ice bath and treated with a large excess of $CH_2N_2$ in $Et_2O$. The excess $CH_2N_2$ was destroyed with glacial AcOH.

The reaction mixture was purified by flash chromatography (10% EtOAc/Hexanes) yielding the compound of Formula 44 (340 rag) (59%). MS(EI) m/e 458 ($M^+$).

EXAMPLE 5

Preparation of Compound of Formula 45 from Compound of Formula 44

(44) $\longrightarrow$  EQCC

-continued

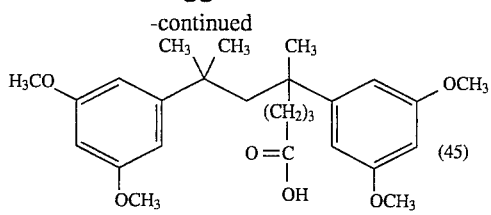

A compound of Formula 44 (1.64 g) was stirred at room temperature under $N_2$ in 20 ml of absolute EtOH and 10 ml of 10% aqueous KOH.

After 16 hours, the solvents were evaporated under high vacuum. The residue was treated with water and acidified with saturated aqueous oxalic acid. The white solid was extracted several times with $CH_2Cl_2$. The combined extracts were washed with water and dried ($Na_2SO_4$). Yield: 1.61 g of the compound of Formula 45. MS(FAB) m/e 445 (M+1).

EXAMPLE 6

Preparation of Compound of Formula 46 from Compound of Formula 45

(45) ⟶ EQDD

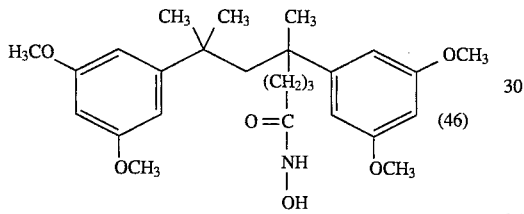

Oxalyl chloride (0.2 ml; 2.3 mmoles) was added slowly dropwise to a precooled (ice bath) dry $CH_2Cl_2$ (4.0 ml) solution of the compound of Formula 45 (0.444 g; 1.0 mmoles) and dry DMF (93 ml; 1.2 mmoles). Vigorous gas evolution occurred. After the addition, the solution was stirred for 30 minutes, then was added via syringe dropwise to a precooled (ice bath) solution of $NH_2OH \cdot HCl$ (0.278 g; 4 mmoles) and $Et_3N$ (6 mmoles; 0.64 ml) in THF (1.5 ml) and water (0.75 ml). After the addition, the solution was stirred in an ice bath for 1½ hours then poured in 5 ml of 3N aqueous HCl. The mixture was extracted with EtOAc. The combined extracts were washed with water and dried. The reaction mixture was purified by flash chromatography (EtOAc) yielding 305 mg (66%) of the compound of Formula 46. MS(FAB) m/e 460 (M+1).

The invention being thus described, it will be obvious that the same may be varied in many ways. Such variations are not to be regarded as a departure from the spirit and scope of the invention and all such modifications are intended to be included within the scope of the claims.

What is claimed is:

1. A compound having the formula 3:

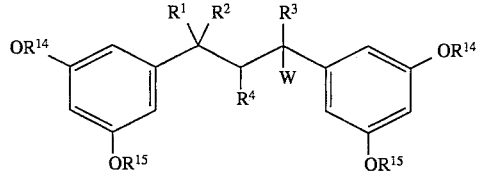

wherein:

$R^1$ and $R^2$ are the same and are alkyl;

$R^3$ is alkyl;

$R^4$ is H;

W is —$(CH_2)_nX$;

n is 3 or 4;

when n is 4, X is —$OR^{10}$ or —$OC(O)R^9$; and when n is 3, then X is —$C(O)R^{11}$, wherein $R^{11}$ is selected from H, OH, —$OCH_3$ and —NHOH;

$R^9$ is selected from H, alkyl, aryl, substituted aryl, aralkyl, cycloalkyl, or heteroaryl, with the proviso that said heteroaryl group is bound through a ring carbon;

$R^{10}$ is selected from H or alkyl: and $R^{14}$ and $R^{15}$ are the same or different and are selected from alkyl.

2. The compound of claim 1 having the formula 4:

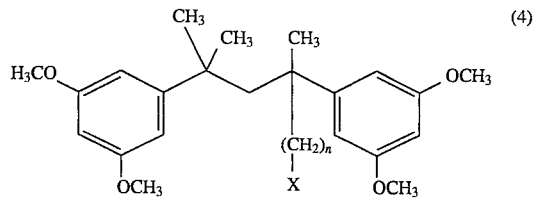

3. The compound of claim 2 having formula 5:

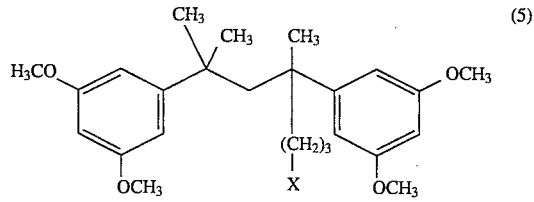

wherein X is selected from —C(O)H, —C(O)OH, —C(O)OCH$_3$, or —C(O)NHOH.

4. The compound of claim 2 having the formula 6:

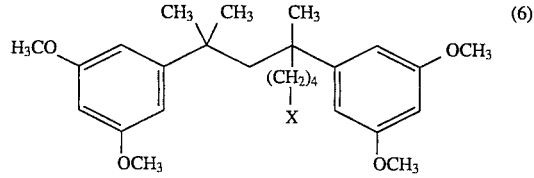

wherein X is —OH or —OC(O)CH$_3$.

5. A method of treating hyperproliferative skin disease in a mammal comprising administering to said mammal an antihyperproliferative effective amount of a compound of claim 3.

6. A method of treating hyperproliferative skin disease in a mammal comprising administering to said mammal an antihyperproliferative effective amount of a compound of claim 4.

7. The compound of claim 3 having a formula selected from:

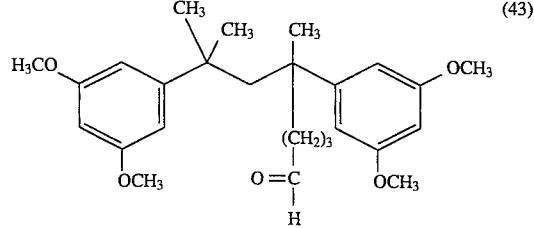

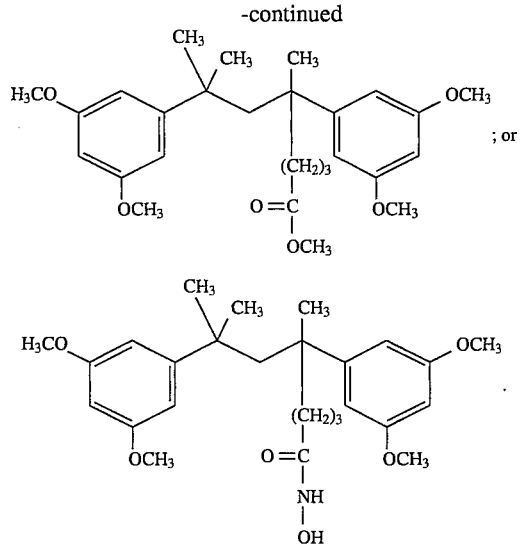

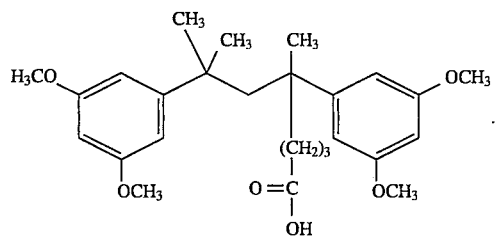

8. The compound of claim 3 having the formula:

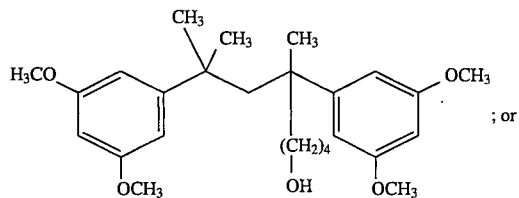

9. The compound of claim 4 having a formula selected from:

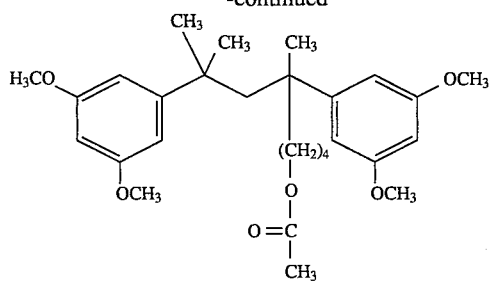

; or

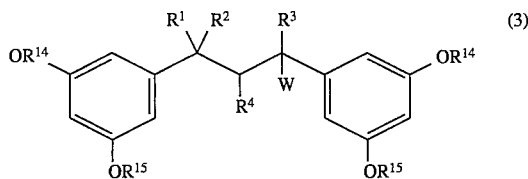

10. A compound of formula 3:

$$\text{(3)}$$

(structure with $OR^{14}$, $OR^{15}$ groups, $R^1$, $R^2$, $R^3$, $R^4$, and W substituents)

wherein:

$R^1$ and $R^2$ are the same and are alkyl;

$R^3$ is alkyl;

$R^4$ is H;

W is —$(CH_2)_nX$;

n is 3 or 4;

when n is 4, X is —$OR^{10}$ or —$OC(O)R^9$; and when n is 3, then X is —$C(O)R^{11}$;

$R^5$ is selected from H, alkyl, aryl, alkaryl, aralkyl, cycloalkyl, or heteroaryl, with the proviso that said heteroaryl group is bound through a ring carbon;

$R^6$ and $R^7$ are the same or different and are selected from H, alkyl, aryl, alkaryl, aralkyl, acyl, substituted aryl, cycloalkyl or heteroaryl, with the proviso that when $R^6$ and/or $R^7$ is a heteroaryl group said heteroaryl group is bound through a ring carbon;

$R^9$ is selected from H, alkyl, aryl, substituted aryl, aralkyl, cycloalkyl, or heteroaryl, with the proviso that said heteroaryl group is bound through a ring carbon;

$R^{10}$ is selected from H or alkyl;

$R^{11}$ is selected from H, —$OR^5$, —$NR^6R^7$, or —$NR^5OH$; and $R^{14}$ and $R^{15}$ are the same or different and are selected from alkyl.

* * * * *